United States Patent
Hart et al.

(10) Patent No.: US 11,548,719 B2
(45) Date of Patent: Jan. 10, 2023

(54) MEDICAL ELECTRODE DISPENSER WITH INDICATORS

(71) Applicant: Conmed Corporation, Utica, NY (US)

(72) Inventors: John E. Hart, Centreville, VA (US); Timothy A. Donaldson, Canton, OH (US)

(73) Assignee: Conmed Corporation, Utica, NY (US)

(*) Notice: Subject to any disclaimer, the term of this patent is extended or adjusted under 35 U.S.C. 154(b) by 0 days.

(21) Appl. No.: 17/287,278

(22) PCT Filed: Oct. 23, 2019

(86) PCT No.: PCT/US2019/057563
§ 371 (c)(1),
(2) Date: Apr. 21, 2021

(87) PCT Pub. No.: WO2020/086661
PCT Pub. Date: Apr. 30, 2020

(65) Prior Publication Data
US 2021/0354905 A1 Nov. 18, 2021

Related U.S. Application Data

(60) Provisional application No. 62/749,146, filed on Oct. 23, 2018.

(51) Int. Cl.
*B65D 83/04* (2006.01)
*A61B 50/30* (2016.01)
(Continued)

(52) U.S. Cl.
CPC .......... *B65D 83/0472* (2013.01); *A61B 50/30* (2016.02); *B65D 73/02* (2013.01); *B65D 85/672* (2013.01)

(58) Field of Classification Search
CPC ........ A61B 50/30; B65D 65/46; B65D 73/02; B65D 83/04; B65D 83/0472; B65D 85/672
See application file for complete search history.

(56) References Cited

U.S. PATENT DOCUMENTS 1,567,991 A * 12/1925 Clark ...................... F42B 3/087
206/459.5
3,861,560 A * 1/1975 Entwistle ................. B65D 5/72
206/409
(Continued)

FOREIGN PATENT DOCUMENTS

CH 687579 1/1997
DE 4324468 5/1994
(Continued)

OTHER PUBLICATIONS

International Search Report Form PCT/ISA/220, International Application No. PCT/US2019/057563, pp. 1-9, dated Jan. 13, 2020.
(Continued)

*Primary Examiner* — Bryon P Gehman
(74) *Attorney, Agent, or Firm* — Bond, Schoeneck & King, PLLC; Frederick J. M. Price

(57) ABSTRACT

A dispenser device for storing and distributing medical electrodes. The dispenser device includes a shell having an inner volume. The shell has an aperture extending through the shell to the inner volume. A strip of a plurality of electrodes is arranged in a pattern within the inner volume of the shell. An end of the strip extends through the aperture and out of the shell. Pulling the end of the strip moves the plurality of electrodes according to the pattern. The shell is preferably a round or rectangular shape. For a round shell, the strip of electrodes is wrapped around a hub within the inner volume. For a rectangular shell, the strip of electrodes is arranged in a Z-fold pattern within the inner volume. The
(Continued)

Figure 1:
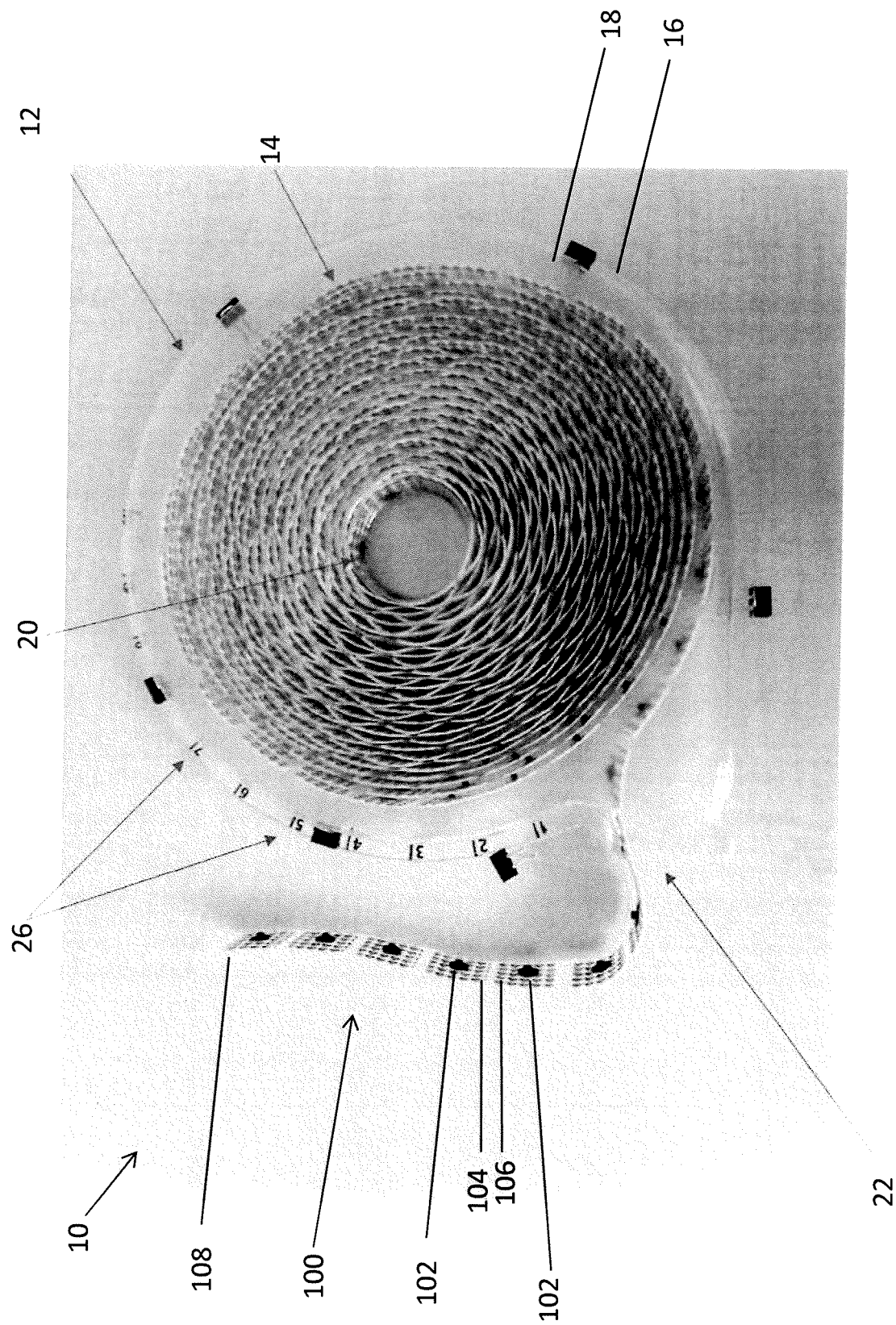

dispenser device may have a vapor proof cap over the aperture that prevents the electrodes from drying out within the shell.

10 Claims, 2 Drawing Sheets

(51) Int. Cl.
*B65D 73/02* (2006.01)
*B65D 85/672* (2006.01)

(56) References Cited

U.S. PATENT DOCUMENTS

| | | | |
|---|---|---|---|
| 4,543,958 A * | 10/1985 | Cartmell | A61B 5/259 |
| | | | 600/397 |
| 5,076,424 A * | 12/1991 | Nakamura | A47K 10/421 |
| | | | 206/409 |
| 5,154,335 A | 10/1992 | Bredow et al. | |
| 5,494,168 A * | 2/1996 | Hart | B65D 85/672 |
| | | | 206/416 |
| 5,978,693 A | 11/1999 | Hamilton et al. | |
| 6,175,753 B1 | 1/2001 | Menkes et al. | |
| 6,201,982 B1 | 3/2001 | Menkes et al. | |
| 6,381,481 B1 | 4/2002 | Levendowski et al. | |
| 7,062,309 B2 | 6/2006 | Ryu et al. | |
| 7,158,822 B2 | 1/2007 | Payne, Jr. | |
| 7,455,451 B2 | 11/2008 | Pearl et al. | |
| 8,020,703 B2 * | 9/2011 | List | B65D 83/0472 |
| | | | 206/370 |
| 8,662,347 B2 | 3/2014 | Coggins et al. | |
| 9,216,851 B2 * | 12/2015 | Coggins | A61B 50/22 |
| 10,456,058 B2 | 10/2019 | Lukoschek et al. | |
| 10,946,196 B2 | 3/2021 | Weisend | |
| 2008/0154112 A1 | 6/2008 | Murphy et al. | |
| 2010/0089937 A1 | 4/2010 | Luciano et al. | |
| 2013/0211223 A1 | 8/2013 | Marcolongo | |
| 2017/0055903 A1 | 3/2017 | Cramer et al. | |

FOREIGN PATENT DOCUMENTS

| | | | |
|---|---|---|---|
| EP | 1541190 | 6/2005 | |
| FR | 2901989 | 12/2007 | |
| GB | 768914 A * | 2/1957 | B65D 83/0472 |
| GB | 1043751 A | 9/1966 | |
| JP | H11-225978 | 12/2004 | |
| JP | 2005-515123 A | 5/2005 | |
| JP | 2016158964 A | 9/2016 | |
| WO | 2012/140629 | 10/2012 | |
| WO | WO2018/116161 | 6/2018 | |

OTHER PUBLICATIONS

CN Office Action, App. No. 201980068609.3, dated Feb. 16, 2022, pp. 1-7.

JP Office Action, App. No. 2021-521848, dated May 10, 2022, pp. 1-8.

* cited by examiner

MEDICAL ELECTRODE DISPENSER WITH INDICATORS

CROSS-REFERENCES TO RELATED APPLICATIONS

This application is a national stage application under 35 U.S.C. 371 based on international patent application PCT/US19/57563 filed on Oct. 23, 2019, which claims priority to U.S. Provisional Patent Application Serial No. 62/749,146 filed on Oct. 23, 2018, the entireties of which are incorporated herein by reference.

BACKGROUND OF THE INVENTION

1. Field of the Invention

The present invention relates to medical electrodes and, more particularly, to a dispenser device for storing and distributing medical electrodes.

2. Description of Related Art

Medical electrodes are typically used in electrocardiography and like diagnostic procedures as well as for long-term monitoring where a patient must be electrically connected to a test or monitoring device. For a given procedure, a patient may require anywhere from two (2) to eleven (11) medical electrodes. Medical electrodes are typically packaged in quantities of three (3), five (5), ten (10), and fifty (50). Often, clinicians will need to open multiple packages of electrodes to get the desired number for a procedure. Frequently, there will be electrodes that go unused when the number of electrodes required is less than the number of electrodes in the package. In addition to sterilization concerns, the extra electrodes are exposed to vapor and other environmental factors that cause the extra electrodes to immediately begin to "dry out" (i.e., the gel or other adhesive material on the electrode begins to dry). As an electrode dries out, the adhesive properties of the electrode decrease and as a result, the electrode loses the ability to attach to a patient. Further, drying out of the electrode can cause increasingly poor signal quality. Therefore, most extra electrodes in a package are discarded. Discarding unused, new electrodes is inefficient in terms of cost, time, and waste.

Therefore, there is a need for a dispenser device for storing and distributing medical electrodes.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to a dispenser device for storing and distributing medical electrodes. According to an aspect, the dispenser device includes a shell having an inner volume. The shell has an aperture extending through the shell to the inner volume. A strip of a plurality of electrodes is arranged in a pattern within the inner volume of the shell. An end of the strip extends through the aperture and out of the shell. Pulling the end of the strip moves the plurality of electrodes according to the pattern.

According to an aspect, the shell is round. A round shell includes a hub within the inner volume. The strip of electrodes is wrapped around the hub in a circular pattern.

According to another aspect, the shell is rectangular. For a rectangular shell, the strip of electrodes is arranged in a Z-fold pattern within the inner volume.

According to yet another aspect, the dispenser device includes a vapor proof cap over the aperture that prevents the electrodes from drying out within the shell.

BRIEF DESCRIPTION OF THE SEVERAL VIEWS OF THE DRAWING(S)

Figure 2:
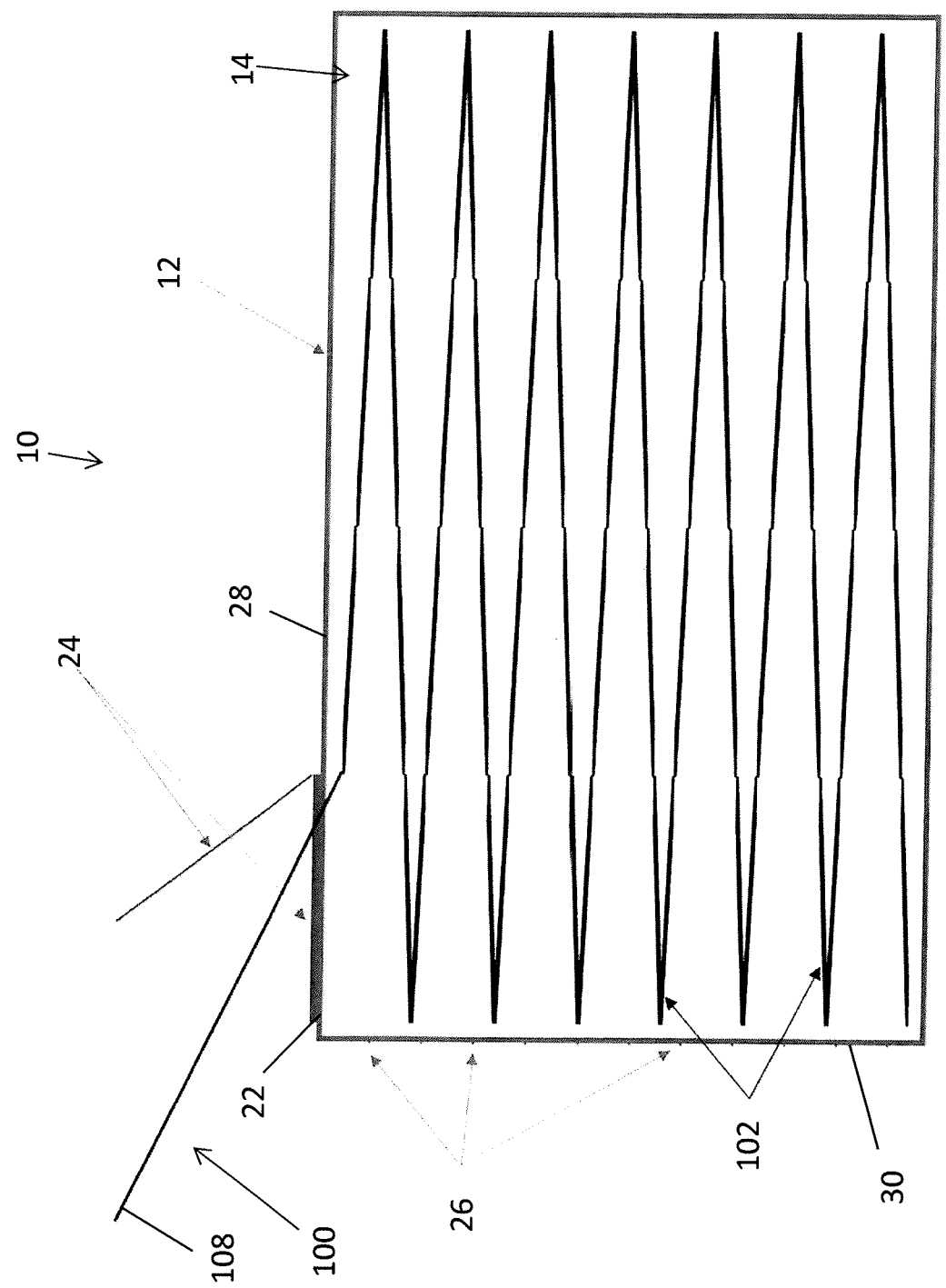

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which:

FIG. 1 is a top view schematic representation of a circular dispenser device, according to an embodiment; and FIG. 2 is a top view schematic representation of a rectangular dispenser device, according to an embodiment.

DETAILED DESCRIPTION OF THE INVENTION

Referring now to the drawings, wherein like reference numerals refer to like parts throughout, there is seen in FIG. 1 a top view schematic representation of a dispenser device 10, according to an embodiment. The dispenser device 10 includes a shell 12 comprising an inner volume 14. In the depicted embodiment, the shell 12 is composed of plastic. The plastic can be clear and/or transparent such that the inner volume 14 is visible. According to an embodiment, the shell 12 is composed of a first portion 16 and a second portion 18 that create the inner volume 14 when connected. In the depicted embodiment, the shell 12 is round or circular. The shell 12 can be fabricated according to methods such as thermoforming.

As shown in FIG. 1, the hollow shell 12 has an integral hub 20 within the inner volume 14. In the embodiment wherein the shell 12 has a first portion 16 and a second portion 18, the hub 20 is attached to and extends from the first portion 16. The hub 20 can extend toward or up to (and connect to) the second portion 18. In FIG. 1, the hub 20 is a circular or round feature. The hub 20 can be hollow (as shown in FIG. 1) or solid. The purpose of the hub 20 is to organize medical electrodes within the inner volume 14 of the shell 12.

Still referring to FIG. 1, medical electrodes 102 are shown within the inner volume 14 of the dispenser device 10. The medical electrodes 102 are connected in a strip 100. Specifically, a first side 104 of a first medical electrode 102 is connected to a second side 106 of an adjacent, second medical electrode 102. To install the strip 100 within the dispenser device 10, the strip 100 of medical electrodes 102 is wrapped around the hub 20 within the inner volume 14 of the shell 12. In the depicted embodiment, the strip 100 of medical electrodes 102 wraps around the hub 20 and rests on the first portion 16 within the inner volume 14 of the shell 12.

With the strip 100 of medical electrodes 102 arranged within the shell 12, the second portion 18 of the shell 12 is connected to the first portion 16 of the shell 12. In a preferred embodiment, the second portion 18 is permanently attached to the first portion 16 in order to protect the medical electrodes 102 from the environmental contaminants. With the strip 100 of medical electrodes 102 wrapped around the hub 20 within the shell 12, an end 108 of the strip 100 extends out from the shell 12, as shown in FIG. 1. The strip 100 is wrapped around the hub 20 such the end 108 of the strip 100 can be pulled to rotate the medical electrodes 102 around the hub 20 within the shell 12.

Specifically, the shell 12 has an aperture 22 for feeding the end 108 of the strip 100 of medical electrodes 102 out from the shell 12. In an embodiment, the dispenser device 10 comprises a cap (not shown) sized and configured to fit over the aperture 22. In a particular embodiment, the cap is a vapor proof cap. The vapor proof cap is releasable such that it allows for a user to pull the strip 100 of medical electrodes 102 out from the shell 12 while limiting the exposure of the medical electrodes 102 to vapor and other environmental elements. The vapor proof cap may be temporarily or permanently connected to the shell 12.

Still referring to FIG. 1, the dispenser device 10 comprises a plurality of indicators 26 on the shell 12. The indicators 26 can be on the first portion 16, the second portion 18, or both the first and second portions 16, 18 of the shell 12. In the depicted embodiment, the indicators 26 extend around the circumference of the shell 12. The indicators 26 can be numbers or some other series of reference markings. The indicators 26 allow a user to determine the number of medical electrodes 102 pulled from the shell 12. In an embodiment wherein the shell 12 is clear (i.e., transparent), when the strip 100 of medical electrodes 102 is pulled out from the shell 12, the user can see the strip 100 of medical electrodes 102 inside the shell 12 as they rotate past the indicators 26. As the medical electrodes 102 rotate past the indicators 26, the user can determine how many medical electrodes 102 are exiting the dispenser device 10.

In an embodiment, the dispenser device 10 includes a cutting feature (not shown). The cutting feature can be located at or near the aperture 22 where the strip 100 of medical electrodes 102 exits the shell 12. The cutting feature can be movable or selectively deployable such that the user can cut the strip 100 of medical electrodes 102 when the desired number of medical electrodes 102 has been pulled from the shell 12.

The medical electrodes 102 can be either pouched or non-pouched. Medical electrodes 102 are pouched when each individual electrode 102 is protected or otherwise covered by an additional material. In the embodiment shown in FIG. 1, the medical electrodes 102 are non-pouched (i.e., not protected or covered by an additional material). If a medical electrode 102 is non-pouched, the inner volume 14 of the shell 12 is preferably coated to prevent vapor transmission into the shell 12. Example coating can include a sprayable metallic or elastomeric impermeable material (as should be understood by a person of ordinary skill in the art in conjunction with a review of this disclosure). As described briefly with reference to the vapor proof cap above, vapor contamination or exposure to the medical electrodes 102 could cause them to dry out.

Turning now to FIG. 2, there is shown a top view schematic representation of the dispenser device 10, according to an alternative embodiment. As shown in FIG. 2, the shell 12 of the dispenser device 10 is rectangular. Although not shown in FIG. 2, the rectangular shell 12 can be composed of a first portion and a second portion with an inner volume 14 therebetween (as described above in conjunction with the embodiment shown in FIG. 1).

A strip 100 of medical electrodes 102 is stored within the inner volume 14 of the rectangular shell 12. However, the rectangular shell 12 embodiment shown in FIG. 2 does not comprise an integral hub 20 as in the circular shell 12 embodiment shown in FIG. 1. Instead, the strip 100 of medical electrodes 102 is arranged in a pattern within the inner volume 14 of the shell 12. As shown in FIG. 2, the strip 100 of medical electrodes 102 is arranged in an alternating pattern, meaning that the strip 100 extends in a first direction and then extends in a second direction. That alternating pattern can be repeated to form the Z-fold (or zigzag) configuration shown in FIG. 2.

The Z-fold configuration of the strip 100 of medical electrodes 102 is preferable for the rectangular shell 12 because it optimizes the space (or size) constrictions of a rectangular-shaped shell 12. As shown in FIG. 2, the strip 100 of medical electrodes 102 extend in a first direction, then in a second direction, and repeat that pathway until an end 108 of the strip 100 of medical electrodes 102 reaches an aperture 22 on a side 28 of the rectangular shell 12. The strip 100 of medical electrodes 102 extends out from the shell 12 through the aperture 22. In an embodiment, the dispenser device 10 comprises a cap 24 sized and configured to fit over the aperture 22. As recited above with reference to the embodiment shown in FIG. 1, the cap 24 can be a releasable vapor proof cap that allows for a user to pull the strip 100 of medical electrodes 102 out from the shell 12, while limiting the exposure of the medical electrodes 102 to vapor and other environmental elements that may dry out or otherwise erode the medical electrodes 102. The vapor proof cap 24 may be temporarily or permanently connected to the rectangular shell 12.

Still referring to FIG. 2, the rectangular shell 12 may also comprise a plurality of indicators 26 extending along at least one side 30 of the rectangular shell 12. As shown in FIG. 2, the indicators 26 extend along the outer perimeter of the side 30 of the shell 12. The indicators 26, as recited above, can be numbers or some other series of reference markings. The indicators 26 allow a user to determine the number of medical electrodes 102 pulled from the shell 12. Specifically, in the embodiment shown in FIG. 2, the strip 100 of medical electrodes 102 is pulled from the aperture 22 and the strip 100 within the inner volume 14 of the shell 12 moves and follows the Z-fold configuration. In an embodiment wherein the rectangular shell 12 is clear (i.e., transparent), the user can see the medical electrodes 102 as they move past the indicators 26 and the user can then determine how many medical electrodes 102 are exiting the dispenser device 10.

In an alternative embodiment, the dispenser device 10 is reusable. In a reusable embodiment, the shell 12 of the dispenser device 10 must be able to move between an open configuration and a closed configuration. In an example, the shell 12 comprises a first portion 16 hingedly connected to a second portion 18 such that the shell 12 can be opened and closed. Numerous other configurations are contemplated that will expose the inner volume 14 of the shell 12 in the open configuration and seal the inner volume 14 of the shell 12 in the closed configuration. In the reusable embodiment, replacement strips 100 of medical electrodes 102 can be obtained separately from the dispenser device 10 and installed into the dispenser device 10 (within the inner volume 14) when the original strip 100 of medical electrodes 102 have been used. A reusable dispenser device 10 reduces waste and potentially reduces storage space if a smaller, fillable shell 12 can be used.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A dispenser device, comprising:
    a shell having an inner volume and an outer circumference;
    a plurality of indicators being disposed on and extending along the shell;
    an aperture extending through the shell to the inner volume;
    a strip of a plurality of electrodes arranged in a circular pattern within the inner volume of the shell, the strip having an end extending through the aperture and out of the shell; and
    wherein pulling the end of the strip moves the plurality of electrodes according to the circular pattern, and wherein the indicators are disposed in a circular pattern to allow a user to determine a number of the plurality of electrodes pulled from the shell.

2. The device of claim 1, further comprising a hub within inner volume of the shell.

3. The device of claim 2, wherein the plurality of electrodes extend circumferentially around the hub.

4. The device of claim 1, further comprising a cap attached to the shell over the aperture.

5. The device of claim 4, wherein the cap is a vapor proof cap.

6. The device of claim 1, wherein the shell is transparent.

7. The device of claim 1, wherein the shell is circular.

8. The device of claim 1, wherein the shell comprises a first portion connected to a second portion.

9. The device of claim 1, wherein the shell is rectangular.

10. The device of claim 9, wherein the plurality of electrodes are arranged in a Z-fold pattern.

\* \* \* \* \*